United States Patent
Chou et al.

(10) Patent No.: US 9,492,707 B2
(45) Date of Patent: Nov. 15, 2016

(54) GOLF CLUB HEAD

(71) Applicant: ADVANCED INTERNATIONAL MULTITECH CO., LTD., Kaohsiung (TW)

(72) Inventors: I-Nan Chou, Kaohsiung (TW); Te-Fu Hsiao, Kaohsiung (TW)

(73) Assignee: ADVANCED INTERNATIONAL MULTITECH CO., LTD., Kaohsuing (TW)

( * ) Notice: Subject to any disclaimer, the term of this patent is extended or adjusted under 35 U.S.C. 154(b) by 0 days.

(21) Appl. No.: 14/746,001

(22) Filed: Jun. 22, 2015

(65) Prior Publication Data

US 2016/0184631 A1 Jun. 30, 2016

(30) Foreign Application Priority Data

Dec. 29, 2014 (TW) .............................. 103146080 A

(51) Int. Cl.
*A63B 24/00* (2006.01)
*A63B 53/04* (2015.01)

(52) U.S. Cl.
CPC ....... *A63B 24/0003* (2013.01); *A63B 53/0466* (2013.01); *A63B 2053/0491* (2013.01)

(58) Field of Classification Search
USPC .................................. 473/221–223, 334–339
See application file for complete search history.

(56) References Cited

U.S. PATENT DOCUMENTS

| | | | | |
|---|---|---|---|---|
| 8,668,595 B2* | 3/2014 | Boyd | ................. | A63B 24/0003 473/223 |
| 8,951,145 B2* | 2/2015 | Bezilla | ................... | A63B 53/04 473/334 |
| 2006/0178229 A1* | 8/2006 | Liang | ................. | A63B 53/0466 473/334 |
| 2016/0074720 A1* | 3/2016 | Kline | ..................... | A63B 53/06 473/223 |

* cited by examiner

*Primary Examiner* — Gene Kim
*Assistant Examiner* — Rayshun Peng
(74) *Attorney, Agent, or Firm* — Muncy, Geissler, Olds & Lowe, P.C.

(57) ABSTRACT

A golf club head includes a head body and a weight-balancing device. The head body is formed with a weighting recess. The weight-balancing device includes a coupling unit having a surrounding wall threadedly engaging the weighting recess, and an intelligent monitoring unit disposed inside the coupling unit. The intelligent monitoring unit includes a shell that is made of a signal-transmittable material and that is partially exposed form the surrounding wall, an intelligent monitoring element that is disposed in the shell and that is operable to detect data related to performance characteristics of a golf swing, and a wireless transmitter that is coupled to the monitoring element and that is operable to output the data.

8 Claims, 4 Drawing Sheets

GOLF CLUB HEAD

CROSS-REFERENCE TO RELATED APPLICATION

This application claims priority of Taiwanese Patent Application No. 103146080, filed on Dec. 29, 2014.

FIELD

The disclosure relates to a golf club head, more particularly to a golf club head having monitoring function.

BACKGROUND

Referring to FIG. 1, PCT Application No. WO2012/149338 discloses a conventional golf club head, which includes a head body 101 formed with a recess 102, a monitoring device 103 installed in the recess 102, a cover plate 104 formed with a through hole 105 corresponding in position to and partially exposing the monitoring device 103, and a screw fastener 106 securing the cover plate 104 to the head body 101. The monitoring device 102 can detect data related to a golfer's swing and transmit the same wirelessly. Although the inclusion of the monitoring device 103 provides an intelligent monitoring function for the conventional golf club head, such configuration of the conventional golf club head provides a relatively weak coupling strength between the monitoring device 103 and the head body 101. In addition, additional processing of the head body 101 may be needed to incorporate the monitoring devices 103 of various sizes.

SUMMARY

Therefore, an object of the disclosure is to provide a golf club head which may alleviate at least one of the aforesaid drawbacks of the prior art.

According to one aspect of the disclosure, a golf club head includes a head body and a weight-balancing device.

The head body is formed with an internally-threaded weighting recess.

The weight-balancing device includes a coupling unit that has a surrounding wall threadedly engaging the weighting recess, and an intelligent monitoring unit that is disposed inside the coupling unit. The intelligent monitoring unit includes a shell, an intelligent monitoring element and a wireless transmitter. The shell is made of a signal-transmittable material and is partially exposed form the surrounding wall of the coupling unit. The shell is interlocked with the surrounding wall for being immobilized relative to the surrounding wall. The intelligent monitoring element is disposed in the shell and is operable to detect data related to performance characteristics of a golf swing. The wireless transmitter is electrically coupled to the monitoring element and is operable to wirelessly output the data detected by the monitoring element.

BRIEF DESCRIPTION OF THE DRAWINGS

Other features and advantages of the disclosure will become apparent in the following detailed description of the exemplary embodiment with reference to the accompanying drawings, of which.

DETAILED DESCRIPTION

Figure 1:
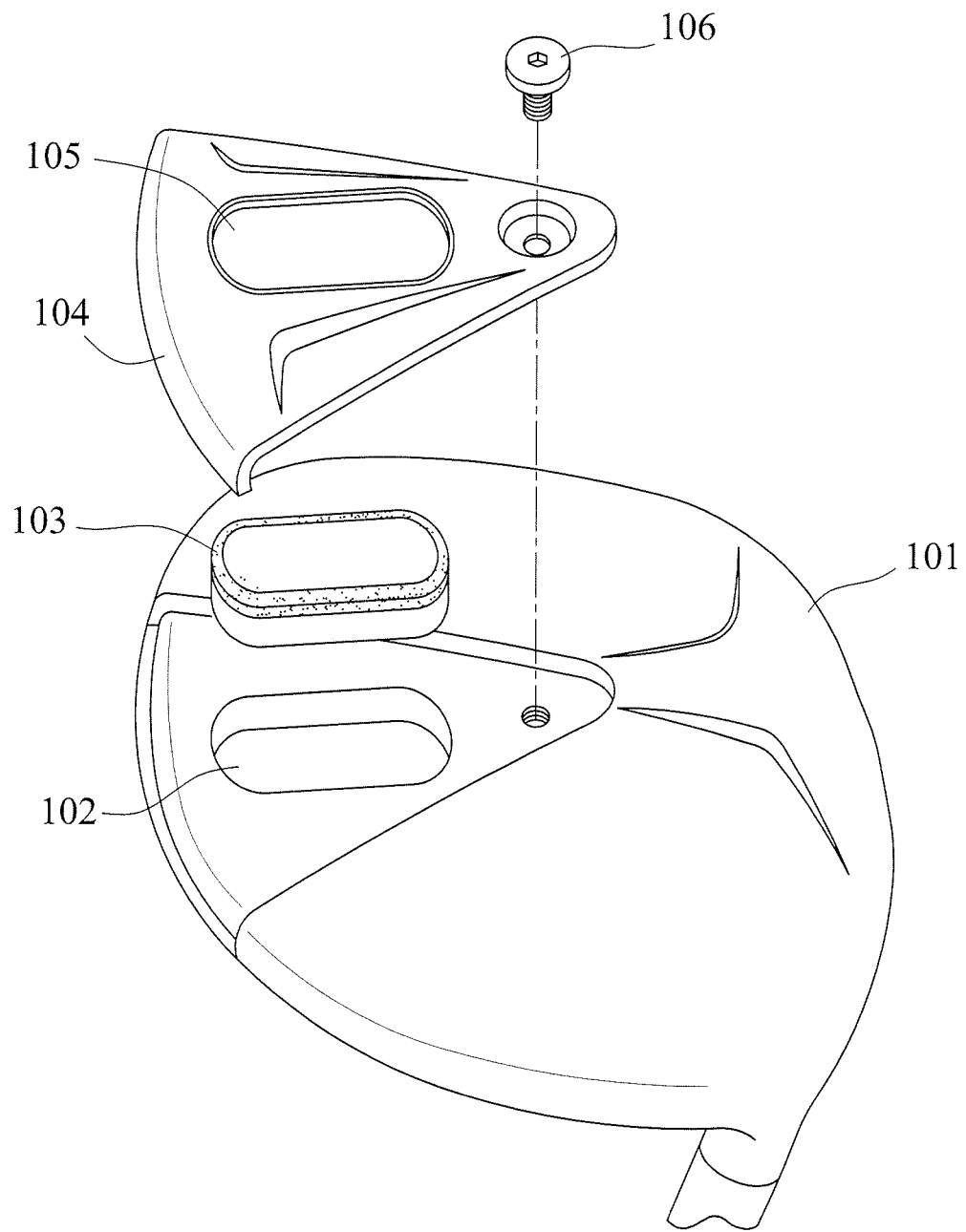
FIG. 1 is an exploded perspective view of a conventional golf club head.
Figure 2:
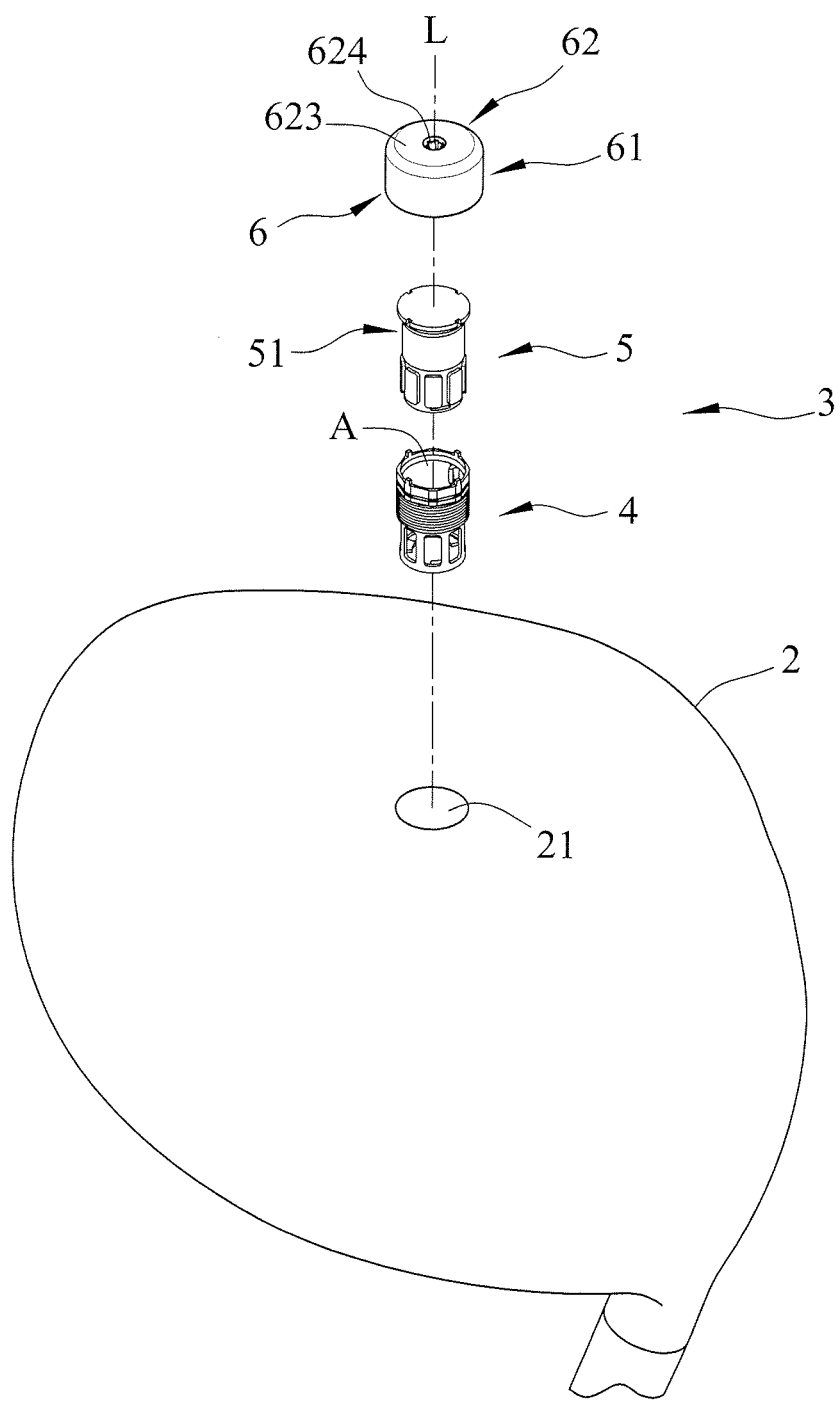
FIG. 2 is an exploded perspective view of an exemplary embodiment of a golf club head according to the present disclosure.
Figure 3:
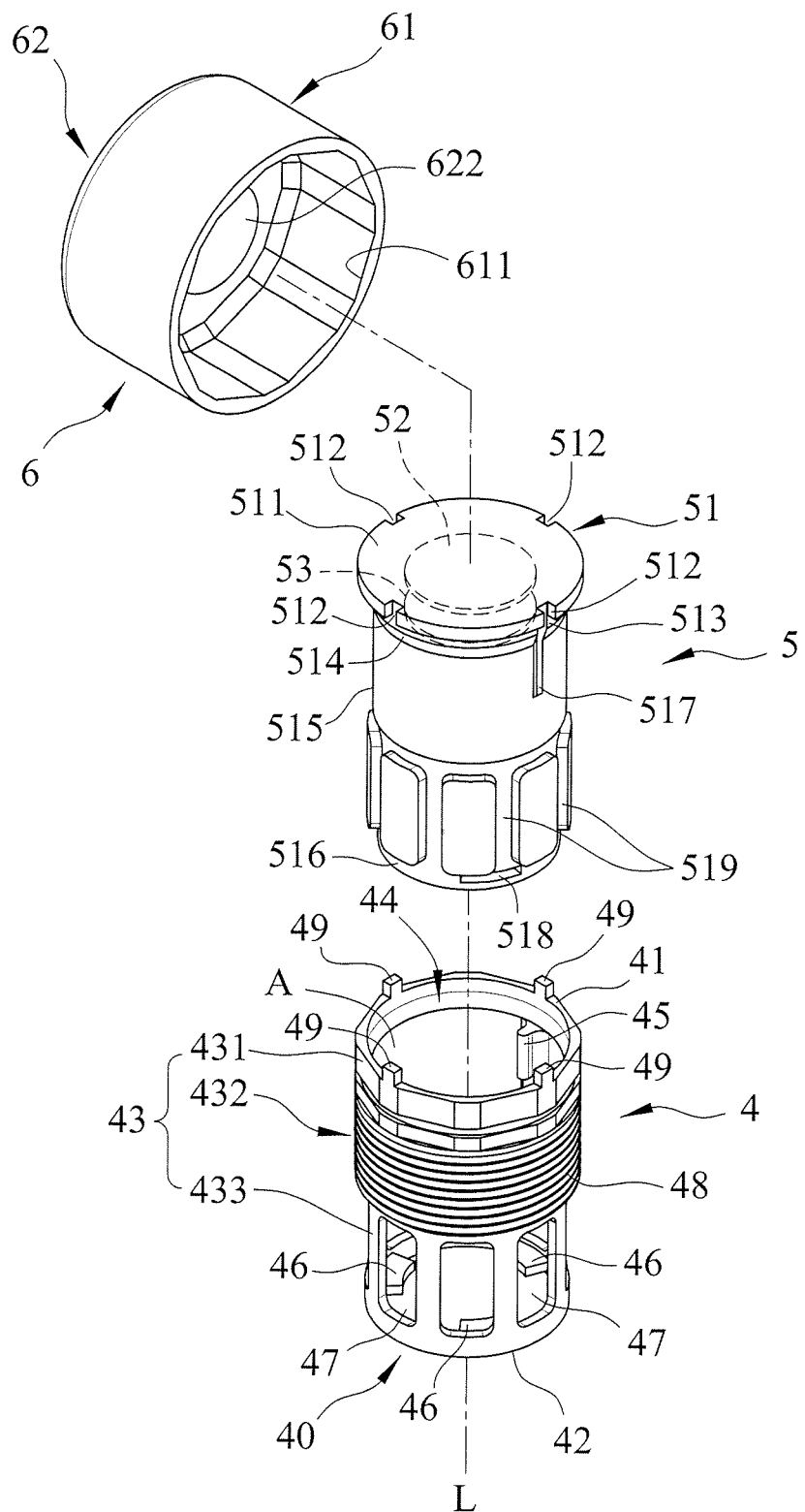
FIG. 3 is an exploded perspective view of the exemplary embodiment, illustrating a weight-balancing device.
Figure 4:
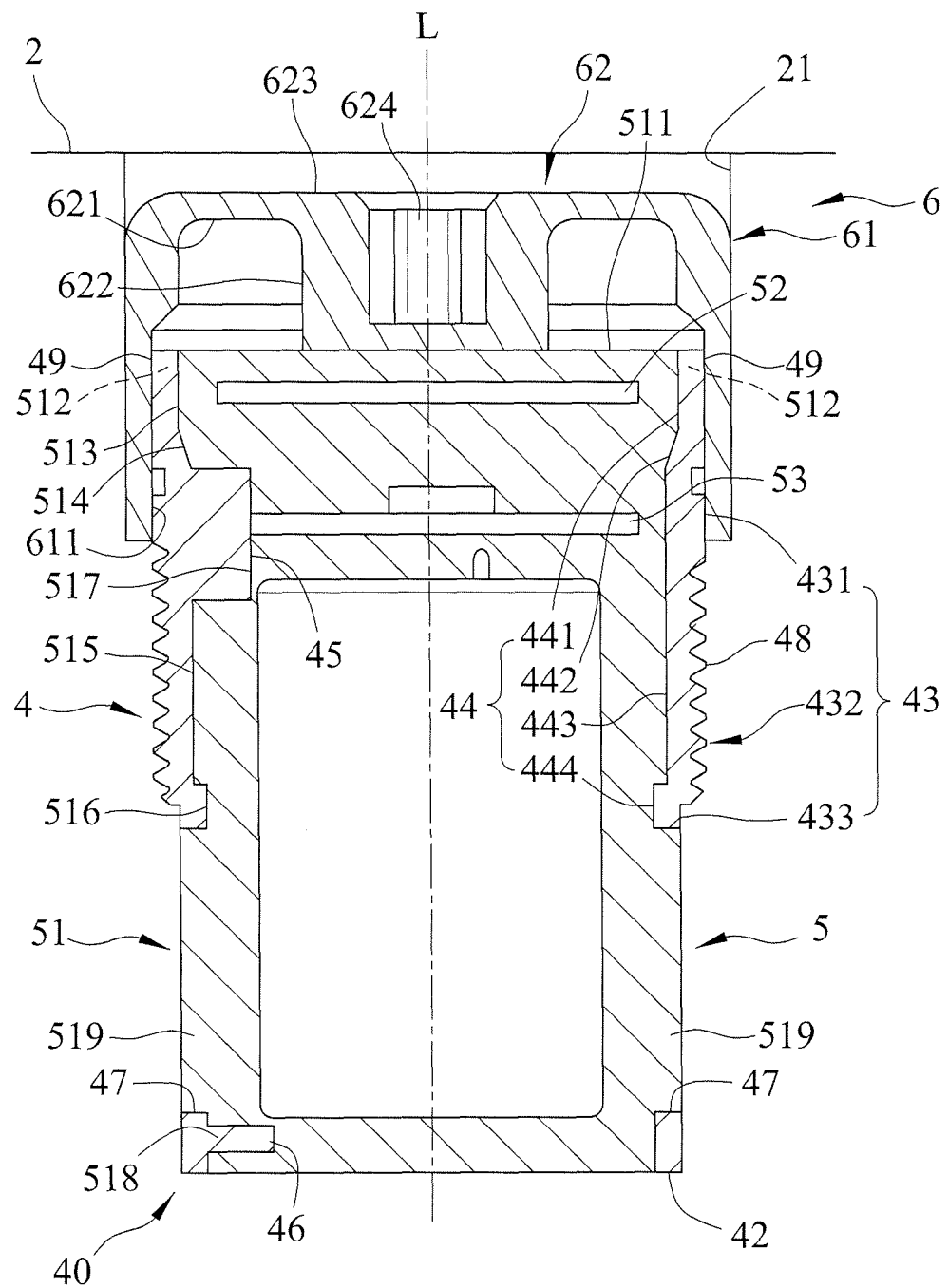
FIG. 4 is a sectional view of the exemplary embodiment, illustrating the weight-balancing device.

Referring to FIGS. 2 to 4, an exemplary embodiment of a golf club head according to the disclosure is shown to include a head body 2 and a weight-balancing device 3.

The head body 2 is formed with an internally-threaded weighting recess 21.

The weight-balancing device 3 includes a coupling unit 4, an intelligent monitoring unit 5 and a cover 6. The coupling unit 4 has a surrounding wall 40 threadedly engaging the weighting recess 21. The intelligent monitoring unit 5 is disposed inside the coupling unit 4. The cover 6 is coupled to the surrounding wall 40 of the coupling unit 4.

The surrounding wall 40 of the coupling unit 4 may be made of a metal material having an electromagnetic interference (EMI) shielding efficiency of less than 80 dB (such as copper, aluminum, nickel and aluminum-magnesium alloy). In this embodiment, the surrounding wall 40 of the coupling unit 4 is made of aluminum-magnesium alloy.

In greater detail, as shown in FIGS. 3 and 4, the surrounding wall 40 surrounds an axis (L) to define a receiving space (A) for receiving the intelligent monitoring unit 5. The surrounding wall 40 has opposite first and second ends 41, 42 that are mutually spaced apart along the axis (L), an outer surrounding surface 43 that interconnects the first and second ends 41, 42, and an inner surrounding surface 44 that is radially opposite to the outer surrounding surface 43. As shown in FIG. 3, the outer surrounding surface 43 of the surrounding wall 40 has a polygonal section 431 that is proximal to the first end 41, a threaded section 432 that is formed with an external thread 48 removably engaging the weighting recess 21 and that is connected to the polygonal section 431, and an extension section 433 that interconnects the threaded section 432 and the second end 42. As shown in FIG. 4, the inner surrounding surface 44 of the surrounding wall 40 has a first surrounding section 441 that is proximal to the first end 41, a tapering section 442 that is connected to and tapered from the first surrounding section 441 toward the second end 42, a second surrounding section 443 that is connected to the tapering section 442, and a third surrounding section 444 that is connected to and projects radially and steppingly from the second surrounding section 443. In this embodiment, the third surrounding section 444 has an inner diameter smaller than that of the second surrounding section 443.

Referring back to FIG. 3, in this embodiment, the first end 41 of the surrounding wall 40 is formed with four protrusions 49 that protrude in direct ions parallel to the axis (L) and that are angularly spaced apart from one another. The inner surrounding surface 44 of the surrounding wall 40 is formed with an alignment piece 45 extending from the tapering section 442 to the second surrounding section 443 in a direction parallel to the axis (L). The third surrounding section 444 of the inner surrounding surface 44 of the surrounding wall 40 is formed with three radially protruding blocks 46 protruding toward the axis (L) and adjacent to the second end 42. The surrounding wall 40 is formed with a plurality of engaging holes 47 which radially penetrate the extension section 433 of the outer surrounding surface 43 and the third surrounding section 444 of the inner surrounding surface 44 and which are disposed between the external thread 48 and the radially protruding blocks 46. It should be noted that the number of the protrusions 49, the radially protruding blocks 46 or the engaging holes 47 is not limited to what is disclosed in this embodiment and may vary (e.g., one, two or more) in other embodiments according to actual requirements.

The intelligent monitoring unit 5 includes a shell 51, an intelligent monitoring element 52 and a wireless transmitter 53. The shell 51 is made of a signal-transmittable material and is received inside the receiving space (A) of the surrounding wall 40 and is partially exposed from the surrounding wall 40. The shell 51 is interlocked with the surrounding wall 40 for being immobilized relative to the surrounding wall 40. The intelligent monitoring element 52 is disposed in the shell 51 and is operable to detect data relative to performance characteristics of a golf swing. The wireless transmitter 53 is electrically coupled to the intelligent monitoring element 52 and is operable to wirelessly output the data detected by the intelligent monitoring element 52.

In greater detail, the shell 51 has a head portion 511 that is partially exposed from the first end 41 of the surrounding wall 40, an extending portion 513 that extends from the head portion 511 along the axis (L) and that is surrounded by the first surrounding section 441 of the inner surrounding surface 44, a converging portion 514 that extends convergingly from the extending portion 513 in a direction away from the head portion 511 along the axis (L) and that is surrounded by the tapering section 442 of the inner surrounding surface 44, a first shank portion 515 that is connected to the converging portion 514 oppositely of the head portion 511 and that is surrounded by the second surrounding section 443 of the inner surrounding surface 44, and a second shank portion 516 that is connected to the first shank portion 515 oppositely of the head portion 511 and that is surrounded by the third surrounding section 444 of the inner surrounding surface 44.

In this embodiment, the shell 51 can be made of a polyurethane based material, a silicone based material, a rubber based material, an epoxy resin based material, an acrylic based material, or a hot melt adhesive material. The head portion 511 of the shell 51 is formed with four first positioning grooves 512 removably and respectively engaged with the protrusions 49 of the surrounding wall 40. An alignment groove 517 is formed and extends from the converging portion 514 to the first shank portion 515 to engage the alignment piece 45 of the surrounding wall 40. The second shank portion 516 is formed with three second positioning grooves 518 (only one is visible from FIG. 3) respectively engaged with the radially protruding blocks 46. The second shank portion 516 is provided with a plurality of engaging blocks 519 that are disposed between the second positioning grooves 518 and the alignment groove 517 and that extend through and engage the engaging holes 47 in the surrounding wall 40, respectively. It should be noted that, the number of the first positioning grooves 512, the second positioning grooves 518, or the engaging blocks 516 is not limited to what is disclosed in this embodiment and may vary in other embodiments according to actual requirements.

The intelligent monitoring element 52 may be operable to detect parameters of a golf swing, such as golf swing speed, golf swing trajectory, ball launch angle, back/down swing speed, back swing angle, attack angle of club head, swing acceleration rate, swing plane, hitting point, driving distance, ball spin rate, ball flight trajectory, etc., and may be operable to record the same for various golf swings. The wireless transmitter 53 is operable to transmit the recorded data by Bluetooth. It is worth noting that the driving distance, the ball spin rate and the ball flight trajectory are obtained through calculation based on other recorded data, i.e., golf swing speed, golf swing trajectory, ball launch angle, back/down swing speed, back swing angle, attack angle of club head, swing acceleration rate, swing plane, and hitting point.

The inclusion of the alignment piece 45 and the alignment groove 517 ensures that the shell 51 is inserted into the receiving space (A) in a preset direction. In addition, engagements between the protrusions 49 and the first positioning grooves 512, between the radially protruding blocks 46 and the second positioning grooves 518, and between the engaging blocks 519 and the engaging holes 47 promote the coupling stability between the shell 51 and the surrounding wall 40 and enables the shell 51 to be interlocked with and immobilized relative to the surrounding wall 40.

The cover 6 includes a tubular wall 61 that interlocks with the polygonal section 431 of the outer surrounding surface 43 of the surrounding wall 40 and that is made of a signal transmittable material (such as Kevlar™ or glass fibers), and a cover plate 62 that is connected to the tubular wall 61. The tubular wall 61 of the cover 6 has an inner surrounding surface 611 matching with the polygonal section 431 of the outer surrounding surface 43 (i.e., the inner surrounding surface 611 of the tubular wall 61 and the polygonal section 431 of the coupling unit 4 are interlockable complementary polygonal surfaces). The cover plate 62 has an inner surface 621 that faces the shell 51, and an outer surface 623 that is opposite to the inner surface 621. The inner surface 621 of the cover plate 62 is formed with an abutment segment 622 protruding therefrom and abutting against the head portion 511 of the shell 51. The cover plate 62 may be formed with a driving part 624 configured to be driven by a driving tool (e.g., a screw driver). In this embodiment, the driving part 624 is indented from the outer surface 623, but in other embodiments the driving part 624 may protrude from the outer surface 623 of the cover plate and is not limited thereto according to the present disclosure. Since the shell 51 is partially exposed from the surrounding wall 40 of the coupling unit 4, the cover 6 made of the signal transmittable material allows the signal outputted by the wireless transmitter 53 in the shell 51 to pass through the cover 6 without being blocked by the surrounding wall 40 of the coupling unit 4. In addition, the cover plate 62 of the cover 6 prevents the intelligent monitoring unit 5 from being directly struck by external objects and causing damage.

Since the golf club head of the present disclosure includes the weight-balancing device 3 which has both weighting and monitoring functions and which can be coupled to the built-in weighting recess 21 of the head body 2, there is no need to conduct additional processing for the head body 2 to form additional recess to receive the monitoring unit (i.e., to incorporate the monitoring function). In addition, the weight-balancing device 3 threadedly engages the weighting recess 21 of the head body 2 utilizing the coupling unit 4 (i.e., the surrounding wall 40), so that the coupling strength therebetween can be enhanced. Moreover, the coupling unit 4 can be easily adjusted (e.g., increasing or decreasing the diameters) to fit into head bodies 2 having weighting recesses 21 of various sizes, resulting in relatively low manufacturing costs.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A golf club head, comprising:
a head body formed with an internally-threaded weighting recess; and
a weight-balancing device including a coupling unit that has a surrounding wall threadedly engaging said weighting recess, and an intelligent monitoring unit that is disposed inside said coupling unit;
wherein said intelligent monitoring unit includes
a shell that is made of a signal-transmittable material and that is partially exposed from said surrounding wall of said coupling unit, said shell being interlocked with said surrounding wall for being immobilized relative to said surrounding wall,
an intelligent monitoring element that is disposed in said shell and that is operable to detect data related to performance characteristics of a golf swing, and
a wireless transmitter that is electrically coupled to said intelligent monitoring element and that is operable to wirelessly output the data detected by said intelligent monitoring element;
wherein said surrounding wall of said coupling unit has opposite first and second ends that are mutually spaced apart along an axis of said surrounding wall, and an outer surrounding surface that interconnects said first and second ends and that is formed with an external thread; and
wherein said shell has a head portion that is partially exposed from said first end of said surrounding wall and that is formed with a first positioning groove, and said first end of said surrounding wall is formed with a protrusion removably engaging said first positioning groove.

2. The golf club head set forth in claim 1, wherein said surrounding wall further has an inner surrounding surface that is opposite to said outer surrounding surface and that is formed with an alignment piece extending in a direction parallel to the axis of said surrounding wall, and said shell is further formed with an alignment groove engaging said alignment piece.

3. The golf club head set forth in claim 2, wherein said inner surrounding surface of said surrounding wall is further formed with a radially protruding block adjacent to said second end, and said shell is further formed with a second positioning groove engaged with said radially protruding block.

4. The golf club head set forth in claim 3, wherein said surrounding wall is formed with an engaging hole penetrating said inner and outer surrounding surfaces, and said shell further has an engaging block that extends through and engages said engaging hole.

5. The golf club head set forth in claim 4, wherein:
said outer surrounding surface of said surrounding wall has a polygonal section that is proximal to said first end, a threaded section that is formed with said external thread and that is connected to said polygonal section, and an extension section that interconnects said threaded section and said second end;
said inner surrounding surface of said surrounding wall has a first surrounding section that is proximal to said first end, a tapering section that is connected to and tapered from said first surrounding section toward said second end, a second surrounding section that is connected to said tapering section, and a third surrounding section that is connected to and projects radially and steppingly from said second surrounding section;
said engaging hole penetrates said extension section of said outer surrounding surface and said third surrounding section of said inner surrounding surface and is disposed between said radially protruding block and said external thread; and
said alignment piece of said surrounding wall extends from said tapering section to said second surrounding section of said inner surrounding surface.

6. The golf club head set forth in claim 5, wherein:
said shell of said intelligent monitoring unit further has
an extending portion that extends from said head portion along the axis and that is surrounded by said first surrounding section of said inner surrounding surface,
a converging portion that extends convergingly from said extending portion in a direction away from said head portion along the axis and that is surrounded by said tapering section of said inner surrounding surface,
a first shank portion that is connected to said converging portion oppositely of said head portion and that is surrounded by said second surrounding section of said inner surrounding surface, and
a second shank portion that is connected to said first shank portion oppositely of said head portion and that is surrounded by said third surrounding section of said inner surrounding surface;
wherein said second positioning groove is formed in said second shank portion, said alignment groove extending from said converging portion to said first shank portion, said engaging block being disposed between said second positioning groove and said alignment groove.

7. The golf club head set forth in claim 6, further comprising a cover coupled to said surrounding wall of said coupling unit and including a tubular wall that interlocks with said polygonal section of said outer surrounding surface and that is made of a signal-transmittable material, and a cover plate that is connected to said tubular wall of said cover, wherein:
said tubular wall of said cover has an inner surrounding surface matching with said polygonal section of said outer surrounding surface of said coupling unit, said inner surrounding surface of said tubular wall and said polygonal section of said outer surrounding surface of said coupling unit being interlockable complementary polygonal surfaces; and
said cover plate has an inner surface that faces said shell and that is formed with an abutment segment protruding from said inner surface of said cover plate and abutting against said head portion of said shell.

8. The golf club head set forth in claim 7, wherein said cover plate further has an outer surface that is opposite to said inner surface of said cover plate and that is formed with a driven part configured to be driven by a driving tool.

* * * * *